(12) United States Patent
Hayenga et al.

(10) Patent No.: US 7,223,371 B2
(45) Date of Patent: May 29, 2007

(54) MICROFLUIDIC CHANNEL NETWORK DEVICE

(75) Inventors: Jon W. Hayenga, Redmond, WA (US);
Bernhard H. Weigl, Seattle, WA (US);
Ronald L. Bardell, St. Louis Park, MN (US); Christopher J. Morris, Redmond, WA (US)

(73) Assignee: Micronics, Inc., Redmond, WA (US)

( * ) Notice: Subject to any disclaimer, the term of this patent is extended or adjusted under 35 U.S.C. 154(b) by 353 days.

(21) Appl. No.: 10/370,433

(22) Filed: Feb. 20, 2003

(65) Prior Publication Data
US 2003/0175990 A1    Sep. 18, 2003

Related U.S. Application Data

(60) Provisional application No. 60/364,343, filed on Mar. 14, 2002.

(51) Int. Cl.
*B01L 3/02* (2006.01)
*B01L 11/00* (2006.01)
*B32B 5/02* (2006.01)
*B32B 27/04* (2006.01)
*B32B 27/12* (2006.01)

(52) U.S. Cl. .......................... 422/100; 422/50; 422/63; 422/68.1; 422/81; 422/82.01; 422/82.05; 422/101; 422/102; 422/103; 422/104; 436/43; 436/52; 436/53; 436/63; 436/149; 436/177; 436/180

(58) Field of Classification Search .................. 422/50, 422/63, 68.1, 81, 82.01, 82.05, 100, 101, 422/102, 103, 104, 82.02; 436/43, 52, 53, 436/63, 149, 164, 174, 177, 180
See application file for complete search history.

(56) References Cited

U.S. PATENT DOCUMENTS 5,716,852 A    2/1998   Yager et al. ................. 436/172
(Continued)

FOREIGN PATENT DOCUMENTS

WO    WO 91/15750    10/1991
(Continued)

OTHER PUBLICATIONS

Blankenstein, G. et al., "Flow Switch for Analyte Injection and Cell/Particle Sorting," in *Proc. of the 2nd International Symposium on Miniaturized Total Analysis System*, μTAS96 (1996), pp. 82-84.
(Continued)

*Primary Examiner*—Brian Sines
(74) *Attorney, Agent, or Firm*—Seed IP Law Group PLLC

(57) ABSTRACT

Described herein is microfluidic device for joining fluids and a related method for doing the same. The device according to the present invention includes a microfluidic junction, an outlet channel, and a plurality of circuit units. A microfluidic junction is an area for converging multiple fluids. An outlet channel is capable of receiving fluid from the microfluidic junction. An outlet channel includes a first end connected with the microfluidic junction, a second end connected with a waste reservoir, and an analysis region positioned between the first end and the second end of the outlet channel. The device also includes a plurality of circuit units. Each circuit unit includes a source channel with a first end capable of receiving sample fluid and a second end connected with the microfluidic junction; a branch channel connected with the source channel at an intersection; and a flow diversion system capable of differentially directing fluid flowing through a source channel either into the microfluidic junction or into a branch channel.

22 Claims, 5 Drawing Sheets

U.S. PATENT DOCUMENTS

| | | | |
|---|---|---|---|
| 5,726,404 A | 3/1998 | Brody | 200/81 R |
| 5,837,200 A | 11/1998 | Diessel et al. | 422/73 |
| 5,858,195 A * | 1/1999 | Ramsey | 204/601 |
| 6,156,270 A | 12/2000 | Buechler | 422/58 |
| 6,270,641 B1 | 8/2001 | Griffiths et al. | 204/451 |
| 6,415,821 B2 * | 7/2002 | Kamholz et al. | 137/827 |
| 6,524,456 B1 * | 2/2003 | Ramsey et al. | 204/450 |
| 6,790,328 B2 * | 9/2004 | Jacobson et al. | 204/453 |
| 2001/0048900 A1 | 12/2001 | Bardell et al. | 422/100 |

FOREIGN PATENT DOCUMENTS

| | | |
|---|---|---|
| WO | WO 97/00442 | 1/1997 |
| WO | WO 99/60397 | 11/1999 |
| WO | WO 02/11888 | 2/2002 |

OTHER PUBLICATIONS

Brody, J.P. et al., "Biotechnology at Low Reynolds Numbers," *Biophysical Journal* 71:3430-3441, Dec. 1996.

* cited by examiner

60

200

MICROFLUIDIC CHANNEL NETWORK DEVICE

CROSS-REFERENCE TO RELATED APPLICATIONS

This application claims priority from U.S. Provisional Patent Application No. 60/364,343, filed Mar. 14, 2002, entitled "Microfluidics Systems and Methods".

FIELD OF THE INVENTION

This invention relates to microfluidic devices and methods for performing analytical testing, and in particular, to a group of devices and methods that use microfluidic technology to join and analyze multiple fluids.

BACKGROUND OF THE INVENTION

Microfluidic devices are becoming increasingly popular for performing analytical testing. Tools developed by the semiconductor industry for miniaturizing electronics enable fabrication and inexpensive mass production of intricate fluid systems. Microfluidic systems are increasingly utilized in performing a variety of analytical techniques for the acquisition of information in multiple disciplines, including the medical field, life sciences, and drug discovery and development.

There are different ways to manufacture microfluidic devices, including traditional lithographic techniques, soft lithography, and laminate technologies. In laminate fabrication the device consists of layers of material or lamina that have been cut, such as by a laser or stamp, into the desired shape and then held together with some form of adhesive, most commonly pressure-sensitive or thermally-activated adhesive. Maylar is commonly used, although other materials such as glass and polydimethylsiloxane (PMDS) have also been successfully incorporated into laminate devices. Microfluidic device construction may include a multi-layer laminated structure where each layer has channels and structures fabricated from a laminate material, forming microscale voids or channels where fluids flow. A microscale channel is generally defined as a fluid passage with at least one internal cross-sectional dimension that is less than 500 micrometers and typically between about 0.1 micrometers and about 500 micrometers. Either external pressurized fluid forced into the laminate or structures located within the laminate affect the control and pumping of fluids through these channels.

Under microfluidic conditions, fluids usually flow in a very predictable, laminar fashion, thereby allowing multiple fluids to flow next to each other in the same channel without turbulent mixing or the need for physical separation by a membrane. This is known as the laminar fluid diffusion interface. Smaller particles typically diffuse quickly across the boundary layer, whereas large molecules and particles, such as cells, typically diffuse only minimally.

U.S. Pat. No. 5,716,852 teaches a method for analyzing the presence and concentration of small particles in a flow cell using laminar flow and diffusion principles. Described is a channel cell system for detecting the presence of analyte particles in a sample stream using a laminar flow channel having at least two inlet means which provide an indicator stream and a sample stream, where the laminar flow channel has a depth sufficiently small to force laminar flow of the streams and length sufficient for diffusion of particles of the analyte into the indicator stream to form a detection area, and having an outlet out of the channel to form a single mixed stream. This device, which is known as a T-Sensor, may contain an external detecting means for detecting diffusion boundries in the indicator stream. This detecting means may be provided by any means known in the art, including optical means such as optical spectroscopy, or absorption spectroscopy of fluorescence.

Special challenges arise in employing devices that utilize the laminar fluid diffusion interface because preservation and maintenance of laminar flow in these devices relies heavily on precisely timed and controlled, as well as reproducible, introduction of several fluids into one channel. For example, fluids moved through multiple channels may converge and may pass through a single channel in a laminar fashion. However, precisely controlling both the timing and the change in volume of fluids entering the junction is generally necessary to prevent fluids from first reaching the outlet channel or obstructing a neighboring inlet channel before converging with other fluids, both of which may disturb laminar flow. Thus, a means of converging multiple fluids as to produce consistent laminar flow while allowing the appropriate control over the timing and the change in volume of converging fluids is desirable.

SUMMARY OF THE INVENTION

In one exemplary embodiment of the invention, the device comprises a microfluidic junction, an outlet channel, and a plurality of circuit units. A microfluidic junction is an area for converging multiple fluids. An outlet channel is capable of receiving fluid from the microfluidic junction. An outlet channel includes a first end connected with the microfluidic junction, a second end connected with a waste reservoir, and an analysis region positioned between the first end and the second end of the outlet channel. The device also includes a plurality of circuit units. Each circuit unit includes a source channel with a first end capable of receiving sample fluid and a second end connected with the microfluidic junction; a branch channel connected with the source channel at an intersection; and a flow diversion system capable of differentially directing fluid flowing through a source channel either into the microfluidic junction or into a branch channel.

A microfluidic junction can include a chamber connected with an outlet channel and a plurality of inlets. The plurality of inlets are typically positioned along the chamber as to alow fluid to enter the chamber without obstructing neighboring inlets. In one example, the cross-sectional area of each inlet increases as progressing toward the center of the chamber. In another example, each inlet is separated by an intermediary region. An intermediary region, for example, may be uniformly convex or may comprise the meeting of two linear surfaces such as to create an edge. In another example, an intermediary region may contain either a hydrophobic or hydrophilic material deposited along its length.

A circuit unit may comprise a valved circuit unit. A valved circuit unit is a circuit unit containing valves. For example, a valved circuit unit may have a first valve positioned along a branch channel of the circuit unit and a second valve positioned along a source channel of the circuit unit. The first and second valves are typically located at, near or proximate to the intersection of the branch channel and the source channel of a given circuit unit. In some instances, valves can be pneumatic valves.

A circuit unit may also comprise a valveless circuit unit, or a circuit unit comprising valveless liquid microswitches.

DETAILED DESCRIPTION OF THE INVENTION

Figure 1:
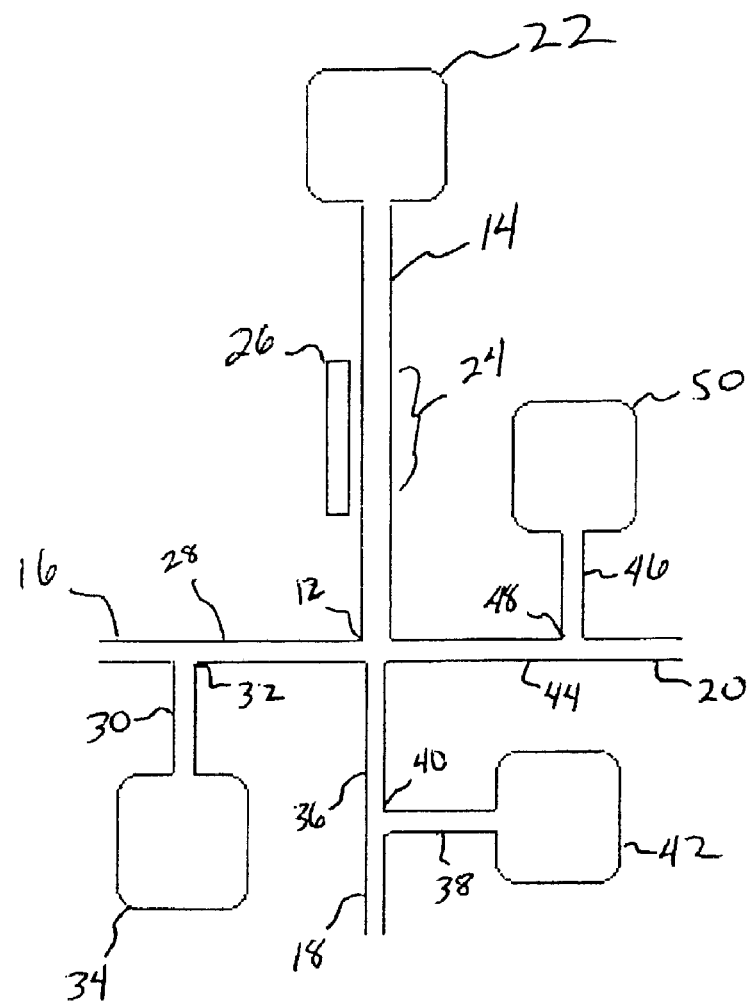
FIG. 1 shows a microfluidic channel network according to the invention.

The invention is illustrated by the following preferred embodiments. In the drawings, like numbers refer to like features, and the same number appearing in more than one drawing refers to the same feature. The members of the flow system of this invention that are "connected" are fluidically connected. The term "between" refers to the fluidic positioning, which does not necessarily correspond to the geometric positioning. The terms "top", "bottom" and "side" refer to the orientation in the drawings, which is not necessarily the orientation of the members in operation.

The term "microfluidic" is generally defined as a substrate having a fluid passage with at least one internal cross-sectional dimension that is less than 500 micrometers and typically between about 0.1 micrometers and about 500 micrometers. The term "channel" as used herein, refers to a microfluidic channel and describes fluid elements dimensioned so that flow therein is substantially laminar.

As used herein, the term "sample" is used in its broadest sense. Sample is meant to include any particles, chemicals, elements, cells, specimen or culture obtained from any source, including without limitation chemical, biological and environmental samples. Sample may be obtained from animals (including humans) and encompass fluids, solids, tissues, and gases. Biological samples include, without limitation, cells and any components thereof, blood products, such as plasma, serum and the like, proteins, peptides, amino acids, polynucleotide, lipids, carbohydrates, and any combinations thereof. The sample may include chemicals, either organic or inorganic, used to interact with the interactive material. When the interactive material contains biological material, for example, drugs, chemicals or other biological molecules may be added to the samples to cause a reaction or response by, among or within the biological material. Environmental samples include environmental material such as surface matter, soil, water, crystals and industrial samples.

Channels and other microfluidic structures can be microfabricated in a substrate to produce a cartridge. As used herein, the term "cartridge" refers to a microfluidic device, which is typically, but not necessarily, disposable and which can be coupled with measurement, pumping, electronic, fluidic or other apparatus. The cartridge can be microfabricated using a variety of methods, including without limitation, traditional lithographic techniques, soft lithography, laminate technologies, etc. For example, the cartridge can be microfabricated from any moldable, machinable or etchable substrate. The term machining as used herein includes, without limitation printing, stamping, cutting and laser ablating. The cartridge can be formed in a single sheet, in a pair of sheets sandwiched together, or in a plurality of sheets laminated together. The term "sheet" refers to any solid substrate, flexible or otherwise. The channels can be etched in a silicon substrate and covered with a cover sheet, which can be a transparent cover sheet. In a multi-layer laminate embodiment, the channel walls are defined by removing material from at least one sheet, thus creating channels and voids, and positioning additional sheets on either side of the altered sheets. Any of the layers can contain fluid channels. In some cases the channel is simply a hole (or fluid via) to route the fluid to the next fluid laminate layer. Any two adjacent laminate layers may be bonded together to form a more complex single part.

Electroosmotic and pressure driven flow are non-limiting examples of methods or systems for flow control. As used herein, the term "flow" refers to any type of movement of a liquid or solid through a microfluidic device or in a method according to the invention. Under microfluidic conditions fluid flow is characterized by a low Reynolds number and is predominately laminar, with any mixing of adjacent fluids being mainly by diffusion. Flow also includes, without limitation, any fluid stream as well as any material, cells or particles moving with, within, or against the fluid stream. Any type of force may be applied in order to provide a flow, including without limitation, pressure, capillary action, magnetic and electromagnetic force, electrophoresis, dielectrophoresis, electroosmosis, optical tweezers, and any combinations thereof.

As used herein, the term "microfluidic junction" refers to an area within a network of microfluidic channels where a plurality of channels join and fluids flowing through the interfacing channels may converge. A microfluidic junction according to the present invention typically comprises a chamber connected with an outlet channel and a plurality of inlets. The plurality of inlets may be positioned along the chamber as to allow fluid to enter the chamber without obstructing neighboring inlets.

The term "outlet channel" as used herein, refers to a channel capable of receiving fluid from the microfluidic junction. An outlet channel comprises a first end connected with a microfluidic junction, a second end connected with a waste reservoir, and an analysis region positioned between the first and second ends of the outlet channel. An analysis region is an area designated for monitoring the interaction of fluids passing through an outlet channel.

As used herein, the term "circuit unit" refers to a series of interconnected channels through which fluid flow may be differentially restricted. A circuit unit comprises a source channel, a branch channel and a flow diversion system. A source channel has a first end capable of receiving sample fluid and a second end connected with a microfluidic junction. A branch channel of a circuit unit is connected with a source channel at an intersection. A flow diversion system is capable of differentially directing fluid flowing through a source channel into either the microfluidic junction or a branch channel, or both. A valved circuit unit, for example, is a circuit unit where the flow diversion system comprises at least two valves positioned at, near or proximate to the intersection of the source channel and the branch channel, and fluid flow is capable of being differentially restricted by the use of the valves.

FIG. 1 illustrates a microfluidic device 10 for joining fluids according to an exemplary embodiment of the present invention. The microfluidic device 10 includes a microfluidic junction 12, an outlet channel 14, and a plurality of circuit units 16, 18, 20. Outlet channel 14 includes a first end connected with microfluidic junction 12, a second end connected with a waste reservoir 22, and an analysis region 24 positioned between the first and second ends of outlet channel 14. A sensor window 26 can be positioned along analysis region 24. Circuit unit 16 includes source channel 28, branch channel 30 and a flow diversion system. Source channel 28 has a first end capable of receiving sample fluid and a second end connected with the junction 12. Branch channel 30 is connected to source channel 28 at an intersection 32. Branch channel 30 is further connected to a waste reservoir 34. A flow diversion system is positioned at, near, or proximate to intersection 32, and is capable of differentially directing fluid flow through source channel 28 and into microfluidic junction 12 or into branch channel 30. Similarly, Circuit unit 18 includes source channel 36, branch channel 38 and a flow diversion system. Source channel 36 has a first end capable of receiving sample fluid and a second end connected with the junction 12. Branch channel 38 is connected to source channel 36 at an intersection 40. Branch channel 38 is further connected to a waste reservoir 42. A flow diversion system is positioned at, near, or proximate to intersection 40, and is capable of differentially directing fluid flow through source channel 36 and into microfluidic junction 12 or into branch channel 38. Likewise, Circuit unit 20 includes source channel 44, branch channel 46 and a flow diversion system. Source channel 44 has a first end capable of receiving sample fluid and a second end connected with the junction 12. Branch channel 46 is connected to source channel 44 at an intersection 48. Branch channel 46 is further connected to a waste reservoir 50. A flow diversion system is positioned at, near, or proximate to intersection 48, and is capable of differentially directing fluid flow through source channel 44 and into microfluidic junction 12 or into branch channel 46.

The operation of the microfluidic device 10 of FIG. 1 is now described. Fluids are respectively entered into circuit units 16, 18, 20. Fluid entered into the first end of source channel 28 flows to the intersection 32 and is directed either to continue through source channel 28 and into microfluidic junction 12 or into branch channel 30. Similarly, fluid entered into the first end of source channel 36 flows to the intersection 40 and is directed either to continue through source channel 36 and into microfluidic junction 12 or into branch channel 38. Likewise, fluid entered into the first end of source channel 44 flows to the intersection 48 and is directed either to continue through source channel 44 and into microfluidic junction 12 or into branch channel 46. Fluids directed toward the junction 12 converge in the junction 12 and flow into the outlet channel 14, through the analysis region 24 and into the waste reservoir 22.

Another exemplary embodiment of the invention is described with reference to FIG. 2, which shows at least a portion of a microfluidic device 60. The device 60 includes a microfluidic junction 62 having a plurality of junction inlets 64, 66, and 68 and an outlet channel 70. The plurality of junction inlets 64, 66, 68 can each receive a fluid from respective source channels 72, 74, 76, connected thereto. Valved circuit units 78, 80, 82 are shown.

Many different types of valves for use in controlling fluids in microfluidic devices have been developed and are contemplated for use in the present invention. For example, U.S. patent application Ser. No. 10/114,890, filed Apr. 3, 2002, and incorporated by reference herein in its entirety for all purposes, describes a pneumatic valve for use in laminated plastic microfluidic structures. Specifically described is a device for controlling flow in microfluidic devices including a first substrate having at least one microfluidic structure manufactured therein, a first flexible sheet placed on top of at least a portion of the microfluidic structure, and a means for creating a pressure differential onto the first flexible sheet such that a portion of the sheet moves in relationship to the microfluidic structure wherein the cross-section of the microfluidic structure is altered at least in one dimension such that the fluid resistance in the microfluidic structure is altered. The described zero or low dead volume valve allows flow through microfluidic channels for use in mixing, dilution, particulate suspension and other techniques necessary for flow control in analytical devices.

In one embodiment of the invention, the valves are pneumatic valves integrated into a cartridge constructed of multiple layers. Where a valve is in a "restricted" status, fluid flow past the valve is negligible. Where a valve is in an "unrestricted" status, fluid flows past the valve essentially unabated. In the operation and function of pneumatic valves, pneumatic pressure controls whether the valve is in a restricted or unrestricted status. Pneumatic air lines deliver such pressure.

Valved circuit unit 78 includes source channel 72, branch channel 84, valve 86, and valve 88. Channel 72 has a first end capable of receiving sample fluid and second end connected with junction 62. Valve 86 is positioned at, near, or proximate to junction 62 and between the first end and second end of channel 72. Channel 84 is connected with channel 72 at an intersection 90. Channel 84 is also connected with channel 92. Valve 88 is positioned along channel 84 at, near, or proximate to intersection 90. In operation, fluid entering channel 72 can flow into intersection 90, into a channel 84 or continue flowing through channel 72 and into junction 62, or both, depending upon the status of valves 86 and 88. When valve 86 is restricted and valve 88 is unrestricted, entering fluid can fill channel 72 up to the position of valve 86. Fluid then can move into channel 84, past valve 88, and into channel 92. When valve 86 is unrestricted and valve 88 is restricted, entering fluid can move through the entire length of channel 72 and enter junction 62.

Similarly, valved circuit unit 80 includes source channel 74, branch channel 94, valve 96, and valve 98. Channel 74 has a first end capable of receiving sample fluid and second end connected with junction 62. Valve 96 is positioned at, near, or proximate to intersection 100 and between the first end and second end of channel 74. Channel 94 is connected with channel 74 at an intersection 100. Channel 94 is also connected with channel 92. Valve 98 is positioned along channel 94 at, near, or proximate to intersection 100. In operation, fluid entering channel 74 can flow into intersection 100, into a channel 94 or continue flowing through channel 74 and into junction 62, or both, depending upon the status of valves 96 and 98. When valve 96 is restricted and valve 98 is unrestricted, entering fluid can fill channel 74 up to the position of valve 96. Fluid then can move into channel 94, past valve 98, and into channel 92. When valve 96 is unrestricted and valve 98 is restricted, entering fluid can move through the entire length of channel 74 and enter junction 62.

Likewise, valved circuit unit 82 includes source channel 76, branch channel 102, valve 104, and valve 106. Channel 76 has a first end capable of receiving sample fluid and second end connected with junction 62. Valve 104 is positioned at, near, or proximate to intersection 108 and between the first end and second end of channel 76. Channel 102 is connected with channel 76 at an intersection 108. Channel 102 is also connected with channel 92. Valve 102 is positioned along channel 102 at, near, or proximate to intersection 108. In operation, fluid entering channel 76 can flow into intersection 108, into a channel 102 or continue flowing through channel 76 and into junction 62, or both, depending upon the status of valves 104 and 106. When valve 104 is restricted and valve 106 is unrestricted, entering fluid can fill channel 76 up to the position of valve 104. Fluid then can move into channel 102, past valve 106, and into channel 92. When valve 104 is unrestricted and valve 106 is restricted, entering fluid can move through the entire length of channel 76 and enter junction 62.

In yet another embodiment of the invention, a flow diversion system comprises valveless circuit units. Valveless circuit units containing valveless liquid microswitches, instead of valves, may be substituted for valved circuit units. For example, U.S. Pat. No. 5,726,404, assigned to Micronics, Inc. and incorporated by reference herein in its entirety for all purposes, describes valveless liquid microswitches and teaches a valveless method and apparatus for high speed switching of liquid flow between intersecting microchannels.

The term microfluidic junction refers to an area within a network of microfluidic channels where two or more channels join and fluids flowing through the interfacing channels may converge. In the exemplary embodiment of FIG. 2, microfluidic junction 62 includes a microfluidic junction chamber 110, connects with outlet channel 70, and a plurality of inlets 64, 66, 68. Inlets 64, 66 and 68 are separated by intermediary regions 112, 114, respectively.

In operation, fluids can enter junction 62 through inlets 64, 66, and 68. As illustrated by $d_1$ and $d_2$, the distance between wall 116 and region 112 increases when progressing from inlet 64 toward the center of microfluidic junction chamber 110. The velocity of a fluid flowing through a channel is related to the volume of the channel and is described as follows: Velocity1/Velocity2=Area2/Area1. As fluid flows through a channel of increasing cross-sectional area, velocity decreases. As fluid entering through inlet 64 fills the space between region 112 and wall 116, the velocity of this entering fluid decreases as the fluid progresses from inlet 64 toward the center of chamber 110. Similarly, the distance between region 112 and region 114 increases when progressing from inlet 66 toward the center of chamber 110. As fluid entering through inlet 66 fills the space between regions 112 and 114, the velocity of this entering fluid decreases as the fluid progresses from inlet 66 toward the center of chamber 25. Likewise, the distance between region 114 and wall 118 increases when progressing from inlet 68 toward the center of chamber 110. As fluid entering through inlet 68 fills the space between region 114 and wall 118, the velocity of this entering fluid decreases as the fluid progresses from inlet 68 toward the center of chamber 110. The described geometrical arrangement of junction 62 facilitates equal filling of chamber 110 and compensates for less than precise control over the timing of fluids entering through inlets 64, 66, 68.

Fluids entering the microfluidic junction 62 from inlets 64, 66, 68 converge along intermediary regions located between the respective junction inlets. For example, the leading edge of fluid entering through inlet 64 and the leading edge of fluid entering through inlet 66 converge along region 112 and the converged fluids fill chamber 110 beginning at region 112 and progressing toward the center of chamber 110. Likewise, the leading edge of fluid entering through inlet 66 and the leading edge of fluid entering through inlet 68 converge along region 114 and these converged fluids fill chamber 110 beginning at region 114 and progressing toward the center of chamber 110. Converged fluids continue filling chamber 110, then flow out of the microfluidic junction 62 through outlet channel 70. Convergence of multiple fluids and filling chamber 110 as described permits convergence of multiple fluids, minimizes gas voids, and facilitates laminar flow.

Figure 2:
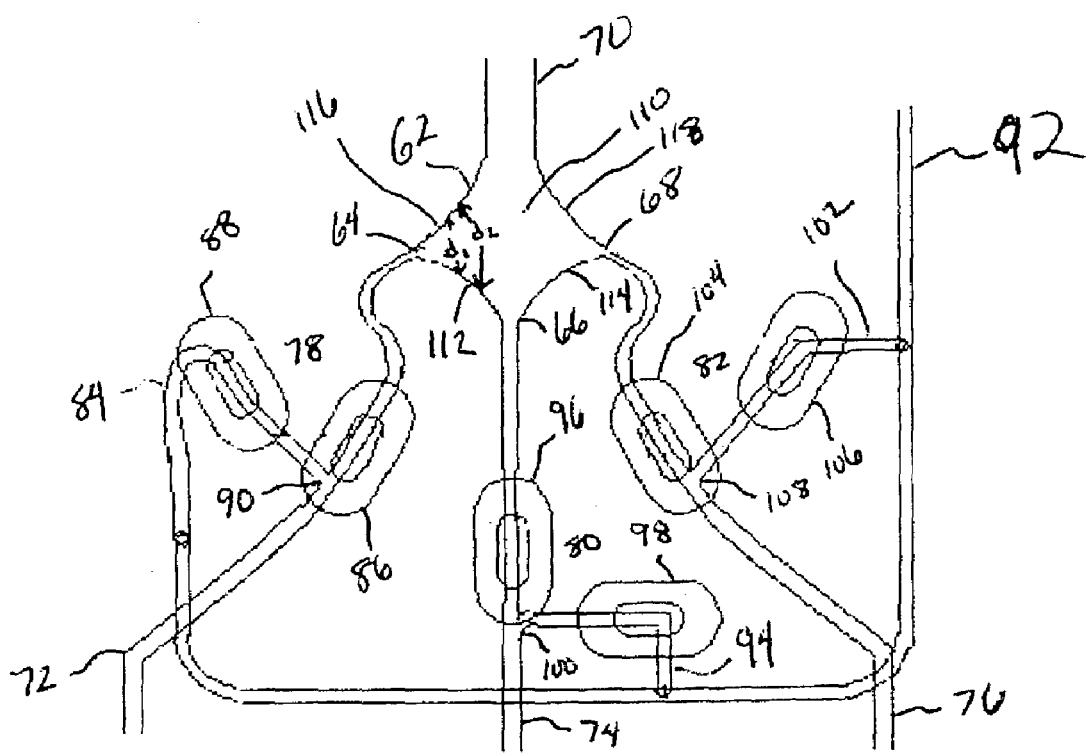
FIG. 2 illustrates a microfluidic channel network for performing a microfluidic process, in accordance with an embodiment of the invention.

In another exemplary embodiment of the invention, an intermediary region may not be uniformly convex as shown in the embodiment of FIG. 2. In another embodiment, an intermediary region may be angled at some position, such as to create an edge. The term "edge" describes the meeting of two linear surfaces, such as to create an angle of less than 180 degrees. Where a fluid moves within a channel due to a positive pressure upstream or a positive displacement, a concave meniscus is formed at the leading edge of the fluid flowing within the channel. When the fluid reaches a portion of the channel containing edges, the resistance against further flow increases and causes the fluid to stop and the meniscus to distend into the open space beyond the sharp edges until the driving pressure exceeds the force needed to overcome the surface tension resistance at the edges. When the force of the driving pressure overcomes the surface tension resistance, the fluid will flow into and thoroughly fill the space in the channel beyond the edges. In yet another embodiment, a hydrophilic or hydrophobic material can be deposited along an intermediary region, depending upon whether the fluid to be deposited in the device is hydrophilic or hydrophobic. Similar to edges, hydrophobic material deposited in a channel causes an increase in surface tension in hydrophilic fluid flowing through the channel. Likewise, hydrophilic material deposited in a channel causes an increase in surface tension in hydrophobic fluid flowing through the channel. The increased resistance causes flowing fluid to stop until the driving pressure overcomes the surface tension resistance.

Figure 3:
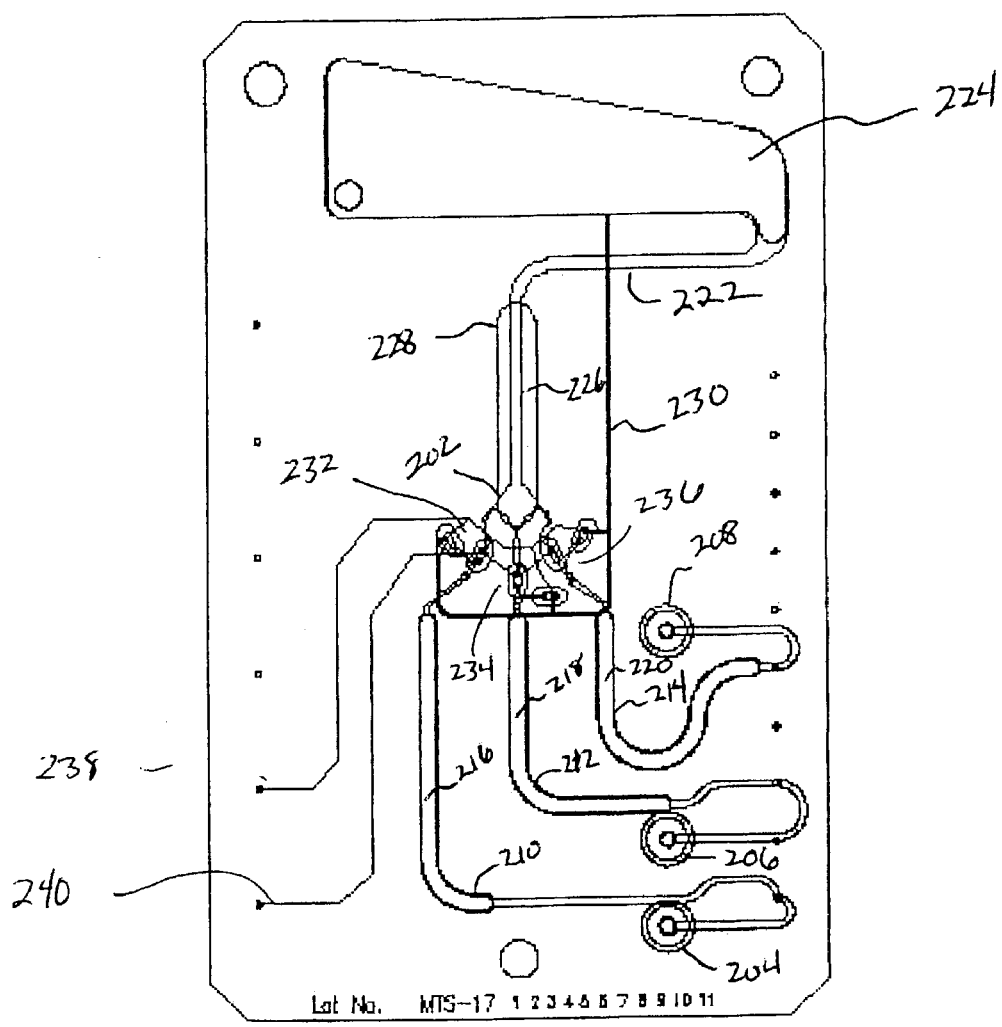
FIG. 3 shows a top view of a cartridge containing a microfluidic channel network for performing a microfluidic process, according to an embodiment of the invention.

FIG. 3 shows a microfluidic device 200 that includes a microfluidic channel network as described in FIG. 1 contained within cartridge, according to another exemplary embodiment of the invention. The device 200 includes a microfluidic junction 202 connected to a plurality of fluid ports 204, 206, 208. The ports 204, 206, 208 here shown are syringe filled fluid ports, but fluid ports that are filled by other means, such as by pipette, may alternatively be used. Source channels 210, 212, 214 are positioned between microfluidic junction 202 and fluid ports 204, 206, and 208, respectively. Source channels 210, 212, 214 respectively include fluid storage loops 216, 218, 220. Fluid storage loops 216, 218, 220 allow on cartridge storage of a greater volume of fluids, but may not be present in alternative embodiments of the invention. Outlet channel 222 has a first end connected with microfluidic junction 202 and a second end connected with waste reservoir 224, and an analysis region 226 positioned between reservoir 224 and junction 202. A sensor window 228 may be positioned along a portion of a channel 222. Analysis region 226 is an area designated for monitoring the interaction of fluids passing in a laminar fashion through a portion of channel 222. An analysis region 226 provides for detection by any means known in the art, for example optical, electrical, pressure sensitive, or flow sensitive detection. More than one detection means can be employed in a single analysis region, for example optical and electrical. For electrical detection, the cartridge can include an electrical interconnect. The cartridge can be electrically connected to electrical meanuring apparatus. For optical detection, a microfluidic device can include a sensor window 228 positioned over the analysis region for optical coupling with measuring apparatus such as light sources and photodetectors. The sensor windows can be inserted glass or if the channel is formed in transparent sheets, the sheets themselves can serve as window. Where the microfluidic device is embodied in a laminate cartridge, a sensor window 228 may include an area of reduced thickness of the laminate cartridge. The optical detection can be absorption, luminescent, fluorescent or scattering based. A microfluidic device can comprise a plurality of analysis regions. Channel 230 is connected with a waste reservoir 224 and with valved circuit units 232, 234, 236, which are structured and operate as described above.

In operation, fluids can be entered into fluid ports 204, 206, 208 and flowed through device 200. Fluid entered into port 204 flows into channel 210 and fills fluid storage loop 216. Depending on the status of the valves of valved circuit unit 232, fluid may be directed into channel 230 and overflow into waste reservoir 224 or may flow into junction 202. Similarly, fluid entered into port 206 flows into channel 212 and fills fluid storage loop 218. Depending on the status of the valves of valved circuit unit 234, fluid may be directed into channel 230 and overflow into waste reservoir 224 or may flow into junction 202. Likewise, fluid entered into port 208 flows into channel 214 and fills fluid storage loop 220. Depending on the status of the valves of valved circuit unit 236, fluid may be directed into channel 230 and overflow into waste reservoir 224 or may flow into junction 202. Fluids from fluid ports 204, 206, 208 converge in junction 202 and flow through channel 222, through analysis region 226 and into waste reservoir 224. Pneumatic air lines 238 and 240 are shown.

Figure 4:
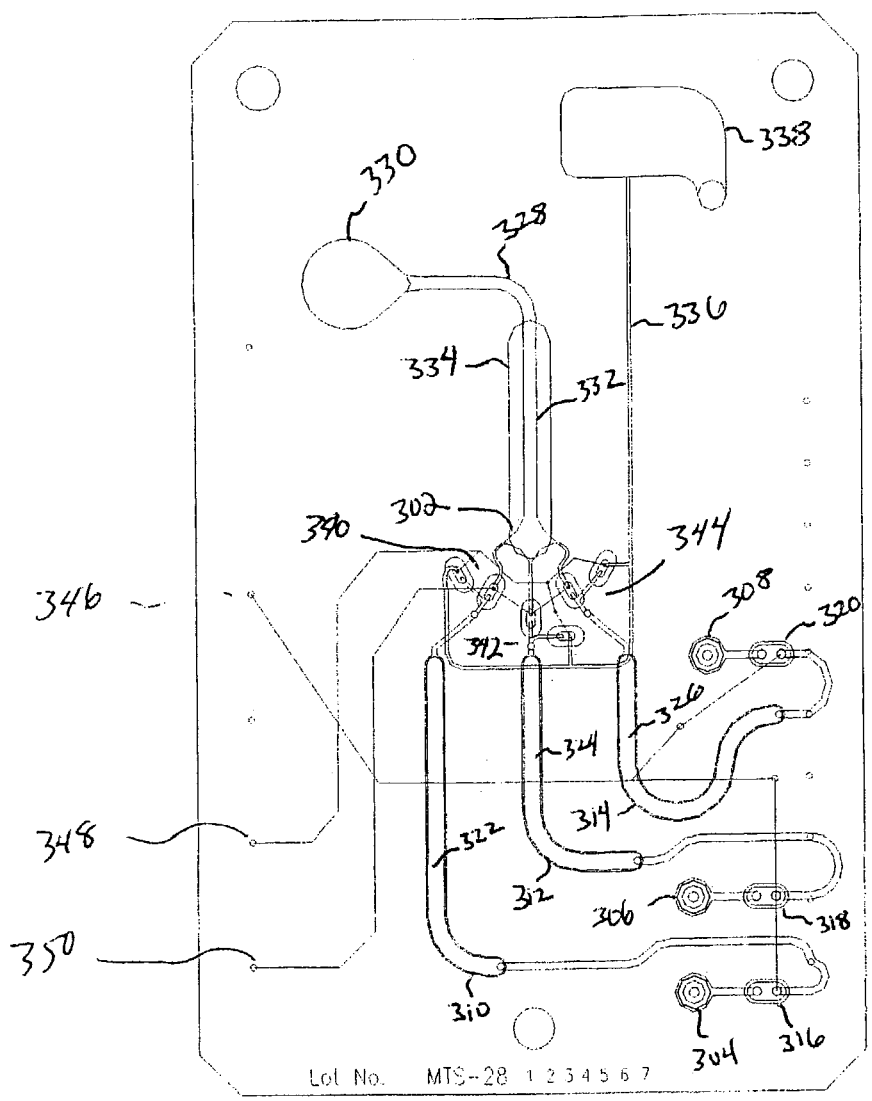
FIG. 4 shows a top view of a cartridge containing a microfluidic channel network for performing a microfluidic process, according to another embodiment of the invention.

FIG. 4 shows a microfluidic device 300 that includes a microfluidic channel network, according to another embodiment of the invention. The microfluidic structure of device 300 is shown contained within a cartridge. The device 300 includes a microfluidic junction 302 connected to a plurality of fluid ports 304, 306, 308. The ports 304, 306, 308 are designed for filling by pipette injection. Source channels 310, 312, 314 are positioned between a microfluidic junction 302 and a plurality of fluid ports 304, 306, and 308, respectively. Channels 310, 312, 314 respectively include valves 316, 318, 320 and fluid storage loops 322, 324, 326. Outlet channel 328 has a first end connected with microfluidic junction 302 and a second end connected with waste reservoir 330, and an analysis region 332 positioned between thereof. A sensor window 334 is positioned along a portion of channel 328. Channel 336 is connected with a waste reservoir 338 and with valved circuit units 340, 342, 344, which are structured and operate as described above.

In operation, fluids can be entered into fluid ports 304, 306, 308 and flowed through device 300. Fluid entered into port 304 flows into channel 310 up to valve 316. If valve 316 is restricted, flow does not continue; if valve 316 is unrestricted fluid continues flowing through channel 310 and into storage loop 322. Depending on the status of the valves of valved circuit unit 340, fluid may be directed into channel 336 and overflow into waste reservoir 338 or may flow into junction 302. Similarly, fluid entered into port 306 flows into channel 312 up to valve 318. If valve 318 is restricted, flow does not continue; if valve 318 is unrestricted fluid continues flowing through channel 312 and into storage loop 324. Depending on the status of the valves of valved circuit unit 342, fluid may be directed into channel 336 and overflow into waste reservoir 338 or may flow into junction 302. Likewise, fluid entered into port 308 flows into channel 314 up to valve 320. If valve 320 is restricted, flow does not continue; if valve 320 is unrestricted fluid continues flowing through channel 314 and into storage loop 326. Depending on the status of the valves of valved circuit unit 344, fluid may be directed into channel 336 and overflow into waste reservoir 338 or may flow into junction 302. Fluids from fluid ports 304, 306, 308 converge in junction 302 and flow through channel 328, past analysis region 332 and into waste reservoir 330. Pneumatic air lines 346, 348, 350 are shown.

Figure 5:
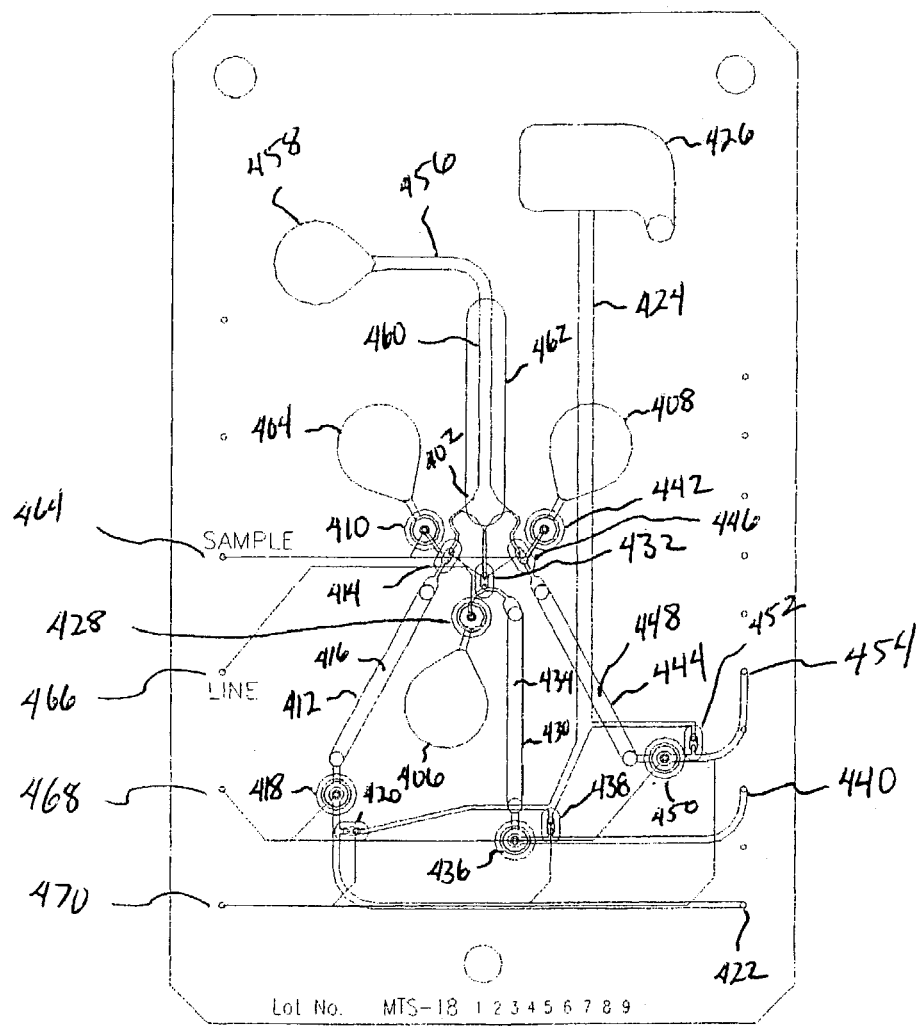
FIG. 5 shows a top view of a cartridge containing a microfluidic channel network for performing a microfluidic process, according to yet another embodiment of the invention.

FIG. 5 shows a microfluidic device 400 according to yet another embodiment of the invention. The microfluidic structure of device 400 is shown contained within a cartridge. The device 400 includes a microfluidic junction 402 connected to a plurality of fluid ports 404, 406, 408. The ports 404, 406, 408 are pipette wells filled by pipette injection. Restriction of valve 410 allows deposition of fluid into port 404 without movement of the fluid into source channel 412. Fluid deposited in port 404 can flow past valves 410, 414 and into source channel 412, including fluid storage loop 416, and down to or past valve 418. Air, fluid or gas contained in the bottom portion of source channel 412 can be cleared where valve 418 is restricted and valve 420 is unrestricted and fluid enters source channel 412 through source 422. Fluid entering from source 422 moves past valve 420, into channel 424 and overflows into waste reservoir 426. After air, fluid or gas is cleared, valves 410, 420 are restricted and valves 414, 418 unrestricted, and fluid in source channel 412 flows toward junction 402.

Similarly, restriction of valve 428 allows deposition of fluid into port 406 without movement of the fluid into channel 430. Fluid deposited in port 406 can flow past valves 428, 432 and into source channel 430, including fluid storage loop 434, and down to or past valve 436. Air, fluid or gas contained in the bottom portion of source channel 430 can be cleared where valve 436 is restricted and valve 438 is unrestricted and fluid enters channel 430 through source 440. Fluid entering from source 440 moves past valve 438, into channel 424 and overflows into waste reservoir 426. After air, fluid or gas is cleared, valves 428, 438 are restricted and valves 432, 436 unrestricted, and fluid in source channel 430 flows toward junction 402.

Likewise, restriction of valve 442 allows deposition of fluid into port 408 without movement of the fluid into source channel 444. Fluid deposited in port 408 can flow past valves 442, 446 and into source channel 444, including fluid storage loop 448, and down to or past valve 450. Air, fluid or gas contained in the bottom portion of source channel 444 can be cleared where valve 450 is restricted and valve 452 is unrestricted and fluid enters channel 444 through source 454. Fluid entering from source 454 moves past valve 452, into channel 424 and overflows into waste reservoir 426. After air, fluid or gas is cleared, valves 442, 452 are restricted and valves 446, 450 unrestricted, and fluid in source channel 444 flows toward junction 404.

Fluids deposited in ports 404, 406, 408 flows through channels 412, 430, 444, respectively, and converge in junction 402. Converging fluids flow in a laminar manner through outlet channel 456 and into waste reservoir 458, including past analysis region 460. Sensor window 462 is positioned along outlet channel 456. Pneumatic air lines 464, 466, 468, 470 are shown.

It should be recognized that other arrangements, configurations and methods should be readily apparent to a person of ordinary skill in the art. Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

What is claimed is:

1. A microfluidic device for joining fluids, comprising:
   a. microfluidic junction;
   b. an outlet channel capable of receiving fluid from the microfluidic junction, said outlet channel comprising a first end connected with the microfluidic junction, a second end connected with a waste reservoir, and an analysis region positioned between said first end and said second end of the outlet channel; and
   c. a plurality of circuit units, each circuit unit comprising:
      i. a source channel with a first end capable of receiving sample fluid and a second end connected with the microfluidic junction;
      ii. a branch channel connected with the source channel at an intersection; and
      iii. a flow diversion system capable of differentially directing fluid flowing through the source channel either into the microfluidic junction or into the branch channel, wherein said microfluidic junction comprises:
         a. a chamber connected with said outlet channel, and
         b. a plurality of inlets positioned along the chamber and capable of allowing fluid to enter the chamber without obstructing neighboring inlets, each of said inlets being separated from a neighboring inlet by an intermediary region, wherein the cross-sectional area of each inlet increases as progressing toward the center of said chamber.

2. The microfluidic device of claim 1, wherein each intermediary region is uniformly convex.

3. The microfluidic device of claim 1, wherein each intermediary region comprises two linear surfaces which meet to form an edge.

4. The microfluidic device of claim 1, wherein a hydrophobic material is deposited along at least one intermediary region.

5. The microfluidic device of claim 1, wherein a hydrophilic material is deposited along at least one intermediary region.

6. The microfluidic device of claim 1, wherein at least one circuit unit is a valved circuit unit comprising a first valve positioned along a branch channel of said valved circuit unit and a second valve positioned along a source channel of said valved circuit unit, said first and second valves being located at, near or proximate to the intersection of said branch channel and said source channel.

7. The microfluidic device of claim 1, wherein at least one circuit unit is a valveless circuit unit comprising a valveless liquid microswitch.

8. The microfluidic device of claim 1, further comprising a plurality of fluid ports for respectively introducing fluid into source channels of said plurality of circuit units, with at least one of said fluid ports being a syringe filled fluid port.

9. The microfluidic device of claim 1, further comprising a plurality of fluid ports for respectively introducing fluid into source channels of said plurality of circuit units, with at least one of said fluid ports being a pipette injection port.

10. The microfluidic device of claim 1, further comprising a plurality of fluid ports for respectively introducing fluid into source channels of said plurality of circuit units, with at least one of said fluid ports being a pipette well filled by pipette injection.

11. The microfluidic device of claim 8, further comprising at least one valve positioned along a source channel, said valve being located between the microfluidic junction and a fluid port.

12. The microfluidic device of claim 9, further comprising at least one valve positioned along a source channel, said valve being located between the microfluidic junction and a fluid port.

13. The microfluidic device of claim 10, further comprising at least one valve positioned along a source channel, said valve being located between the microfluidic junction and a fluid port.

14. The microfluidic device of claim 1, wherein said microfluidic junction, outlet channel and plurality of circuit units are contained within a plurality of laminate layers.

15. A method of joining fluids comprising:
   a. providing a microfluidic device, comprising:
      i. a microfluidic junction;
      ii. an outlet channel capable of receiving fluid from the microfluidic junction, said outlet channel comprising a first end connected with the microfluidic junction, a second end connected with a waste reservoir, and an analysis region positioned between said first end and said second end of the outlet channel;
      iii. a plurality of circuit units, each circuit unit comprising:
         1. a source channel with a first end capable of receiving sample fluid and a second end connected with the microfluidic junction;
         2. a branch channel connected with the source channel at an intersection; and
         3. a flow diversion system capable of differentially directing fluid flowing through a source channel either into the microfluidic junction or into a branch channel;
   b. introducing fluids into the respective source channels of circuit units of the microfluidic device;
   c. flowing fluids into the microfluidic junction of the device; and
   d. flowing fluids through the outlet channel of the microfluidic device,
   wherein the microfluidic junction of said device comprises:
      a. a chamber connected with said outlet channel; and
      b. a plurality of inlets positioned along the chamber and capable of allowing fluid to enter the chamber without obstructing neighboring inlets, each of said inlets being separated from a neighboring inlet by an intermediary region.

16. The method of claim 15, wherein the cross-sectional area of each inlet increases as progressing toward the center of said chamber.

17. The method of claim 15, wherein each intermediary region is uniformly convex.

18. The method of claim 15, wherein each intermediary region comprises two linear surfaces which meet to form an edge.

19. The method of claim 15, wherein a hydrophobic material is deposited along at least one intermediary region.

20. The method of claim 15, wherein a hydrophilic material is deposited along at least one intermediary region.

21. The method of claim 15, wherein at least one circuit unit is a valved circuit unit comprising a first valve positioned along a branch channel of said valved circuit unit and a second valve positioned along a source channel of said valved circuit unit, said first and second valves being located at, near or proximate to the intersection of said branch channel and said source channel.

22. The method of claim 15, wherein at least one circuit unit is a valveless circuit unit comprising a valveless liquid microswitch.

* * * * *